(12) United States Patent
Vanpoulle et al.

(10) Patent No.: US 9,980,480 B2
(45) Date of Patent: May 29, 2018

(54) BIOCIDAL ROOFING GRANULES, ROOFING PRODUCTS INCLUDING SUCH GRANULES, AND PROCESS FOR PREPARING SAME

(75) Inventors: Sophie Vanpoulle, Gentilly (FR); Van Nhan Nguyen, Paris (FR); Alexandra Dekoninck, Ezanville (FR)

(73) Assignee: CertainTeed Corporation, Malvern, PA (US)

(*) Notice: Subject to any disclaimer, the term of this patent is extended or adjusted under 35 U.S.C. 154(b) by 1353 days.

(21) Appl. No.: 13/348,028

(22) Filed: Jan. 11, 2012

(65) Prior Publication Data

US 2012/0107500 A1 May 3, 2012

Related U.S. Application Data

(60) Division of application No. 11/830,580, filed on Jul. 30, 2007, which is a continuation-in-part of
(Continued)

(51) Int. Cl.
*B05D 7/00* (2006.01)
*A01N 25/12* (2006.01)
(Continued)

(52) U.S. Cl.
CPC ............ *A01N 25/12* (2013.01); *A01N 25/34* (2013.01); *C09C 1/0081* (2013.01); *C09C 3/006* (2013.01); *C09C 3/063* (2013.01); *C09C 3/08* (2013.01); *C09C 3/12* (2013.01); *E04D 13/002* (2013.01); *C01P 2006/12* (2013.01); *C01P 2006/14* (2013.01); *E04D 2001/005* (2013.01); *Y10T 428/2438* (2015.01); *Y10T 428/24372* (2015.01); *Y10T 428/24388* (2015.01)

(58) Field of Classification Search
CPC ................................ A01N 25/34; C09C 3/063
USPC ......................................................... 427/212
See application file for complete search history.

(56) References Cited

U.S. PATENT DOCUMENTS

| 1,943,525 A | 1/1934 | Gundlach |
| 2,057,677 A | 10/1936 | Gundlach |

(Continued)

FOREIGN PATENT DOCUMENTS

| CA | 1122897 | 5/1982 |
| EP | 0903389 | 3/1999 |

(Continued)

OTHER PUBLICATIONS

Pei, Effect of drying on the mesoporous structure of sol-derived silica with PPO-PEO-PPO template block copolymer, Journal of Colloid and Interface Science, vol. 284, Issue 1, p. 222-227, Nov. 25, 2004.*

(Continued)

*Primary Examiner* — Tabatha Penny
(74) *Attorney, Agent, or Firm* — McDonnell Boehnen Hulbert & Berghoff LLP

(57) ABSTRACT

Biocidal roofing granules are prepared by providing a mineral core and at least one biocidal photocatalytic metal oxide. A gel-forming inorganic coating medium is prepared and used to coat the mineral core to form a coating layer having a porous network on the mineral core, and the at least one biocidal photocatalytic metal oxide is disposed in the porous network.

31 Claims, 4 Drawing Sheets

Related U.S. Application Data application No. PCT/FR2006/050296, filed on Apr. 4, 2006.

(51) Int. Cl.

| | |
|---|---|
| A01N 25/34 | (2006.01) |
| C09C 1/00 | (2006.01) |
| C09C 3/00 | (2006.01) |
| C09C 3/06 | (2006.01) |
| C09C 3/08 | (2006.01) |
| C09C 3/12 | (2006.01) |
| E04D 13/00 | (2006.01) |
| E04D 1/00 | (2006.01) |

(56) References Cited

U.S. PATENT DOCUMENTS

| | | |
|---|---|---|
| 2,057,678 A | 10/1936 | Gundlach |
| 2,057,679 A | 10/1936 | Gundlach |
| 2,133,728 A | 10/1938 | Teetor |
| 2,379,358 A | 6/1945 | Jewett |
| 2,417,058 A | 3/1947 | Buzzell et al. |
| 2,591,149 A | 4/1952 | Grove |
| 2,614,051 A | 10/1952 | Buzzell et al. |
| 2,695,851 A | 11/1954 | Lodge |
| 2,732,311 A | 1/1956 | Hartwright |
| 2,898,232 A | 8/1959 | Miller et al. |
| 2,927,045 A | 3/1960 | Lodge et al. |
| 2,963,378 A | 12/1960 | Palmquist et al. |
| 2,981,636 A | 4/1961 | Lodge et al. |
| 2,986,476 A | 5/1961 | Larrsen |
| 3,225,031 A | 12/1965 | Sherlock |
| 3,507,676 A | 4/1970 | McMahon |
| 4,038,239 A | 7/1977 | Coyner et al. |
| 4,092,441 A | 5/1978 | Meyer et al. |
| 4,218,502 A | 8/1980 | Graham et al. |
| 4,234,639 A | 11/1980 | Graham et al. |
| 4,287,248 A | 9/1981 | Gessner et al. |
| 4,378,408 A | 3/1983 | Joedicke |
| 4,504,402 A | 3/1985 | Chen et al. |
| 4,583,486 A | 4/1986 | Miller |
| 4,708,812 A | 11/1987 | Hatfield |
| 4,717,614 A | 1/1988 | Bondoc et al. |
| 4,916,014 A | 4/1990 | Weber et al. |
| 4,945,945 A | 8/1990 | Schmid |
| 5,000,999 A | 3/1991 | Hollander |
| 5,194,113 A | 3/1993 | Lasch et al. |
| 5,240,760 A | 8/1993 | George et al. |
| 5,245,850 A | 9/1993 | Kugler |
| 5,310,803 A | 5/1994 | Hansen |
| 5,356,664 A | 10/1994 | Narayan et al. |
| 5,380,552 A | 1/1995 | George et al. |
| 5,382,475 A | 1/1995 | Kayser |
| 5,411,803 A | 5/1995 | George et al. |
| 5,427,793 A | 6/1995 | Bigham et al. |
| 5,456,785 A | 10/1995 | Venable |
| 5,484,477 A | 1/1996 | George et al. |
| 5,514,350 A | 5/1996 | Kear et al. |
| 5,516,573 A | 5/1996 | George et al. |
| 5,541,350 A | 7/1996 | Murata et al. |
| 5,573,782 A | 11/1996 | Bigham et al. |
| 5,595,813 A | 1/1997 | Ogawa et al. |
| 5,611,829 A * | 3/1997 | Monroe et al. ............ 51/309 |
| 5,616,532 A | 4/1997 | Heller et al. |
| 5,620,554 A | 4/1997 | Venable |
| 5,643,399 A | 7/1997 | Venable |
| 5,688,592 A | 11/1997 | Shibahashi et al. |
| 5,723,516 A | 3/1998 | Bigham et al. |
| 5,731,369 A | 3/1998 | Mahoney |
| 5,770,295 A | 6/1998 | Alderman |
| 5,783,506 A | 7/1998 | Eppler et al. |
| 5,795,389 A | 8/1998 | Koschitzky |
| 5,840,111 A | 11/1998 | Wiederhoft et al. |
| 5,876,683 A | 3/1999 | Glumac et al. |
| 5,928,761 A | 7/1999 | Hedblom et al. |
| 5,962,143 A | 10/1999 | Krauthauser et al. |
| 5,976,627 A | 11/1999 | Wynne |
| 6,037,289 A | 3/2000 | Chopin et al. |
| 6,063,312 A | 5/2000 | Mannheimer |
| 6,124,466 A | 9/2000 | Matsuno et al. |
| 6,143,318 A | 11/2000 | Gilchrist et al. |
| 6,156,245 A | 12/2000 | Takebayashi et al. |
| 6,174,360 B1 | 1/2001 | Sliwinski et al. |
| 6,214,466 B1 | 4/2001 | Joedicke |
| 6,217,252 B1 | 4/2001 | Tolliver et al. |
| 6,245,381 B1 | 6/2001 | Israel |
| 6,296,912 B1 | 10/2001 | Zickell |
| 6,362,121 B1 | 2/2002 | Chopin et al. |
| 6,355,309 B1 | 3/2002 | Fleming et al. |
| 6,366,397 B1 | 4/2002 | Genjima et al. |
| 6,376,075 B1 | 4/2002 | Tacke-Willemsen et al. |
| 6,413,581 B1 | 4/2002 | Greenberg et al. |
| 6,426,309 B1 | 7/2002 | Miller et al. |
| 6,446,402 B1 | 9/2002 | Byker et al. |
| 6,454,848 B2 | 9/2002 | Sliwinski et al. |
| 6,465,088 B1 | 10/2002 | Talpaert et al. |
| 6,500,555 B1 | 12/2002 | Khaldi |
| 6,502,360 B2 | 1/2003 | Carr, III et al. |
| 6,521,038 B2 | 2/2003 | Yangimoto et al. |
| 6,531,200 B2 | 3/2003 | Zickell et al. |
| 6,533,961 B2 | 3/2003 | Harelstad et al. |
| 6,537,703 B2 | 3/2003 | DuPasquier et al. |
| 6,548,145 B2 | 4/2003 | Joedicke |
| 6,569,520 B1 | 5/2003 | Jacobs |
| 6,572,748 B1 | 6/2003 | Coombs et al. |
| 6,572,784 B1 | 6/2003 | Coombs et al. |
| 6,596,070 B1 | 7/2003 | Schmidt et al. |
| 6,599,355 B1 | 7/2003 | Schmidt et al. |
| 6,607,781 B2 | 8/2003 | Joedicke |
| 6,610,135 B1 | 8/2003 | Ohmori et al. |
| 6,647,688 B1 | 11/2003 | Gaiten et al. |
| 6,653,356 B2 | 11/2003 | Sherman |
| 6,680,134 B2 | 1/2004 | Maurer et al. |
| 6,692,824 B2 | 2/2004 | Benz et al. |
| 6,703,127 B2 | 3/2004 | Davis et al. |
| 6,761,761 B1 | 7/2004 | Schilling et al. |
| 6,797,277 B2 | 9/2004 | Heier et al. |
| 6,861,145 B2 | 3/2005 | Nastke et al. |
| 6,881,701 B2 | 4/2005 | Jacobs |
| 6,881,702 B2 | 4/2005 | Arnold et al. |
| 6,905,698 B1 | 6/2005 | Aldcroft et al. |
| 6,933,007 B2 | 8/2005 | Fensel et al. |
| 7,060,658 B2 | 6/2006 | Joedicke |
| 7,070,843 B2 | 7/2006 | Bartek et al. |
| 7,070,844 B2 | 7/2006 | Bartek |
| 7,132,143 B2 | 11/2006 | Zanchetta et al. |
| 7,176,245 B2 | 2/2007 | Stucky et al. |
| 7,238,408 B2 | 7/2007 | Aschenbeck et al. |
| 7,241,500 B2 | 7/2007 | Shiao et al. |
| 7,335,419 B2 | 2/2008 | Azari et al. |
| 7,442,989 B2 | 9/2008 | Kalkanoglu et al. |
| 7,452,598 B2 | 11/2008 | Shiao et al. |
| 7,592,066 B2 | 9/2009 | Shiao et al. |
| 7,749,583 B2 | 7/2010 | Kalkanoglu et al. |
| 8,114,516 B2 | 2/2012 | Shiao et al. |
| 2002/0009622 A1 | 1/2002 | Goodson |
| 2002/0066233 A1* | 6/2002 | McArdle et al. ............ 51/308 |
| 2002/0092596 A1 | 7/2002 | Phillips et al. |
| 2002/0160151 A1 | 10/2002 | Pinault et al. |
| 2002/0182334 A1* | 12/2002 | Marzolin et al. ............ 427/421 |
| 2003/0035972 A1 | 2/2003 | Hanson et al. |
| 2003/0044525 A1 | 3/2003 | Aschenbeck |
| 2003/0068469 A1 | 4/2003 | Aschenbeck et al. |
| 2003/0091795 A1 | 5/2003 | Kiik et al. |
| 2003/0091814 A1 | 5/2003 | Benz et al. |
| 2003/0152747 A1 | 8/2003 | Fensel et al. |
| 2003/0203145 A1 | 10/2003 | Zanchetta et al. |
| 2003/0219563 A1 | 11/2003 | Zanchetta et al. |
| 2004/0009313 A1 | 1/2004 | Jackson et al. |
| 2004/0076826 A1 | 4/2004 | Lee |
| 2004/0096586 A1 | 5/2004 | Schulberg et al. |
| 2004/0109985 A1 | 6/2004 | Furst |
| 2004/0110639 A1 | 6/2004 | Joedicke |
| 2004/0170806 A1 | 9/2004 | Hittle et al. |

(56) References Cited

U.S. PATENT DOCUMENTS

| | | | |
|---|---|---|---|
| 2004/0255548 A1* | 12/2004 | Hong et al. | 52/747.1 |
| 2004/0258835 A1 | 12/2004 | Hong et al. | |
| 2005/0053745 A1 | 3/2005 | Bartek et al. | |
| 2005/0053746 A1 | 3/2005 | Bartek | |
| 2005/0064175 A1 | 3/2005 | Azari et al. | |
| 2005/0072110 A1 | 4/2005 | Shiao et al. | |
| 2005/0072114 A1 | 4/2005 | Shiao et al. | |
| 2005/0123611 A1 | 6/2005 | Barbe et al. | |
| 2005/0164880 A1 | 7/2005 | Gesenhues et al. | |
| 2006/0099397 A1 | 5/2006 | Thierauf et al. | |
| 2006/0110996 A1 | 5/2006 | Getlichermann et al. | |
| 2006/0243388 A1 | 11/2006 | Kubiak et al. | |
| 2006/0251807 A1 | 11/2006 | Hong et al. | |
| 2007/0065640 A1 | 3/2007 | Joedicke | |
| 2007/0065641 A1 | 3/2007 | Joedicke | |
| 2008/0006323 A1 | 1/2008 | Kalkanoglu et al. | |
| 2008/0008832 A1 | 1/2008 | Shiao et al. | |
| 2008/0008857 A1 | 1/2008 | Kalkanoglu et al. | |
| 2008/0008858 A1 | 1/2008 | Hong et al. | |
| 2008/0115444 A1 | 5/2008 | Kalkanoglu et al. | |
| 2008/0118640 A1 | 5/2008 | Kalkanoglu et al. | |
| 2008/0131616 A1 | 6/2008 | Besson et al. | |
| 2008/0131664 A1 | 6/2008 | Teng et al. | |
| 2008/0248241 A1 | 10/2008 | Kalkanoglu et al. | |
| 2008/0248242 A1 | 10/2008 | Shaio et al. | |
| 2008/0248244 A1 | 10/2008 | Kalkanoglu et al. | |
| 2008/0248246 A1 | 10/2008 | Shiao et al. | |
| 2008/0277056 A1 | 11/2008 | Kalkanoglu et al. | |
| 2010/0151199 A1 | 6/2010 | Shiao et al. | |
| 2010/0203336 A1 | 8/2010 | Shiao et al. | |
| 2010/0225988 A1 | 9/2010 | Kalkanoglu et al. | |
| 2010/0303875 A1 | 12/2010 | Vanpoullet et al. | |
| 2011/0008622 A1 | 1/2011 | Kalkanoglu et al. | |
| 2011/0027533 A1 | 2/2011 | Kennedy et al. | |
| 2011/0159240 A1 | 6/2011 | Shiao et al. | |
| 2011/0223385 A1 | 9/2011 | Shiao et al. | |
| 2011/0235153 A1 | 9/2011 | Kalkanoglu et al. | |
| 2012/0094076 A1 | 4/2012 | Shiao et al. | |
| 2012/0157583 A1 | 6/2012 | Shiao et al. | |

FOREIGN PATENT DOCUMENTS

| | | |
|---|---|---|
| EP | 15330027 | 8/2004 |
| EP | 0003302 | 6/2008 |
| GB | 1214816 | 2/1970 |
| JP | 61176501 | 8/1986 |
| JP | 4352701 | 12/1992 |
| JP | 2001170553 | 6/2001 |
| JP | 2004162482 | 6/2004 |
| WO | 9423580 | 10/1994 |
| WO | 0011949 | 3/2000 |
| WO | 2007088213 | 8/2007 |

OTHER PUBLICATIONS

Adobe Systems Inc., Technical Guides "Color Models, CIELAB" 2 pgs., 2000.
Adobe Systems Inc., Technical Guides "Color Models, The CIE Color Models," 2 pgs., 2000.
Adobe Systems Inc., Technical Guides "Color Models, CIEXYZ," 2 pgs. 2000.
Adobe Systems Inc., Technical Guides "Color Models, The Munsell Color System," 4 pgs. 2000.
BASF Aktiengesellschaft, "Product Specification, SIXOLUX Metal Gloss L 6015," 1 pg. Sep. 18, 2002.
BASF Aktiengesellschaft, "Product Specification, SIXOLUX Copper Gloss L 3015," 1 pg., Sep. 18, 2002.
BASF Corporation, BASF Launches Two New Pigments for Tile Coatings, by BASF Corp., 1 pg. 1988-2003.
Ferro Corporation, "Cool Colors & Eclipse Heat and Energy Saving Pigments," 2 pgs., 1999-2003.
Ferro Corporation, "How Cool Colors & Eclipse Work," 3 pgs., 2003.
G. Beestman "Microencapsulation of Solid Particles," (H. B. Scher, Ed., Marcel Deeker, Inc., pp. 31-54, New York.
Gaco Western Inc., "Solar Reflectivity of Common Roofing Materials and GACOFlex Roof Coatings," 2 pgs., undated.
Gifty Osei-Premple, et al. "Systhesis and Application of Fluorocarbon Functionalized Mesoporous Silica," Abstract 574e AICHE 2006.
H. Akabari, "Cool Colored Materials for Roofs," Lawrence Radiation Laboratory, Presented at Emerging Technologies in Energy Efficiency Summit 2004, San Francisco, CA Oct. 14, 2004.
Sung, et al., "Characterization of Coating Microstructure Using Laser Scanning Confocal Microscopy," Polymer Materials, Science and Engineering, 83, 243-244, 2000.
L. Sung, et al., "Characterization of Coating Microstucture Using Laser Scanning Confocal Microscopy," undated.
Ming-Zhi Yin, et al., "A Novel Fabrication of Meso-porous Silica Film by Sol-gel of TEOS," Journal of Zhejiang University Science, 422-427 (2004).
Projected Advisory Committee Meeting, "Development of Cool Colored Roofing materials," Oak Ridge National Laboratory and Livermore Berkeley National Laboratory, 55 pgs., Mar. 11, 2003.
Qingyuan-Hu, "Synthesis and Characterization of Functionalized Mesoporous Silica by Aerosol-Assisted Self-Assembly," Abstract 574F, AICHE (2006).
Rhonda Stroud, "Silica Sol as Nanoglue," Naval Research Laboratory, APS (Mar. 2000).
Silberline Manufacturing Co., Inc., "StarBrite," 1 pg., 2003.
T. A. Germer, et al. "Modeling the Appearance of Special Effect Pigment Coatings," Surface Scattering and Diffraction for Advance Metrology, Proc., SPIE 4447, 77-96, 2001.
Y. Jiang, et al, "Novel Pigment Approaches in Optically Variable Security Inks Including Polarizing Cholesteric liquid Crystal (CLC) Polymers," Optical Security and Counterfeit Deterrence Techniques IV, SPIE 4677, 2000.

* cited by examiner

BIOCIDAL ROOFING GRANULES, ROOFING PRODUCTS INCLUDING SUCH GRANULES, AND PROCESS FOR PREPARING SAME

CROSS-REFERENCE TO RELATED APPLICATIONS

The present application is a division of pending U.S. patent application Ser. No. 11/830,580, filed Jul. 30, 2007; which is a continuation-in-part of International Application No. PCT/FR2006/050296, filed Apr. 4, 2006, and designating the United States, which application claims the priority of French Patent Application No. 05 50 899 filed Apr. 7, 2005.

BACKGROUND OF THE INVENTION

1. Field of the Invention

The present invention refers to roofing granules and roofing products having biocidal activity.

2. Brief Description of the Prior Art

Asphalt shingles are conventionally used in the United States and Canada as roofing and siding materials.

Asphalt shingles can be classified into two types of shingles according to the nature of the reinforcement. "Organic" shingles contain cellulose or wood fiber as a thick fiber felt. "Glass fiber" shingles contain a nonwoven mat of glass fibers held together by a binder that is insoluble in water.

In the manufacture of organic shingles, a continuous web of organic fiber felt is fed from a supply roll to an accumulating device made up of several rollers, and then immersed in a first liquid asphalt bath having a temperature of about 250° C. After leaving the first liquid asphalt bath, the felt passes through a second accumulating device so that the felt can absorb excess asphalt and cool slightly. The so-impregnated felt is then coated with molten asphalt on each of its two faces, which ultimately become respectively the upper and lower faces of the web. Roofing granules are distributed on the upper face, and an anti-adhesive agent, for example, talc, is applied to the lower face. The resulting web passes between the rollers of a cold calendar so as to partially embed the roofing granules in the hot asphalt layer on the upper face of the web, and the subsequently cooled product is collected in the form of rolls or of sheets cut to the desired dimensions.

Except for the first stage of impregnation, which is omitted, the manufacture of the glass fiber shingles is carried out in the same way.

In the shingle, the asphalt functions principally to make material impervious to water. It is also used to support the granules and to give strength to the material. The highly ductile character of the asphalt-impregnated felt makes it possible to obtain a flexible product. In general, the longevity of the shingle increases with the quantity of asphalt employed.

The roofing granules, in general formed from mineral materials, serve to provide the shingle with durability. They protect the asphalt from the effects of solar radiation (in particular from the degradative effects of ultraviolet rays) and of the environment (wind, precipitation, pollution, and the like), and contribute to better reflection of incident radiation. The granules, moreover, are typically colored, naturally or artificially by way of the application of pigments, to meet the aesthetic requirements of the user.

However, it is not unusual to see unattractive green, brown or black spots appearing on the surface of asphalt shingles of buildings located in temperate climates. These spots are due to microorganisms, mainly algae of the *Gloeocapsa* genus, which benefit from conditions favorable to their growth found in temperate climates. These conditions include heat, moisture and nutrients. The essential biogenic salts may be provided by the mineral granules themselves, but also may be supplied by organic matter which settles on the shingles. The unattractiveness of these spots, all the more noticeable when the color of the shingle is a light one, is not the only disadvantage. In addition, the resulting darkening of the surface causes an increase in the absorption of the solar radiation, which in turn reduces the effectiveness of the shingles as thermal insulation, and decreases its service life.

To address this problem, algae-contaminated shingles can be treated with suitable biocides. However, the complete elimination of the algae is difficult, and requires the treatment of the entire building, including seemingly healthy surfaces. Even by using a powerful biocide such as sodium hypochlorite, the prophylactic effect is not permanent, because the roof is subsequently scrubbed by weather-borne water. Moreover, certain green algae particularly resistant to biocides can re-colonize previously treated surfaces, thus requiring additional treatments, at regular intervals, to limit their reappearance.

Other methods known to prevent the appearance of the undesirable algae growth are based on the incorporation of algaecide in the shingle. For example, it has been suggested that granules include metal compounds in the form of zinc oxide or sulfide (U.S. Pat. No. 3,507,676), or copper oxide (U.S. Pat. No. 5,356,664), or that a mixture of copper oxide and zinc oxide (U.S. Patent Publication 2002/0258835 and U.S. Patent Publication 2002/0255548) be incorporated in the asphalt.

It has also been suggested to disperse a granular or pulverulent material containing an algaecide on the surface of the shingle (JP-A-2004162482).

U.S. Pat. No. 6,245,381 suggests adding a biocide in the form of salt or of chelate starting from $Cu^{2+}$, $Zn^{2+}$ and $Sn^{2+}$ ions complexed with an organic binder anion in asphalt during the manufacture of the shingle.

Another approach has been to employ photocatalytic particles as biocidal agents. The photocatalytic effect has been employed to provide self-cleaning glass and other ceramic materials. For example, U.S. Pat. No. 6,037,289 discloses a substrate provided with photocatalytic anatase titanium dioxide that is at least partially crystalline, and has a mean size of between 5 and 80 nm. The coating can include an inorganic binder, such as an amorphous or partially crystalline oxide, or a mixture of oxides, such as oxides of silicon, titanium, tin, zirconium or aluminum, which can serve as a matrix for the photocatalytic titanium oxide. Alternatively, a partly organic binder can be used, such as a binder based on epoxide-containing alkoxysilanes. Similarly, U.S. Pat. No. 6,465,088 discloses a substrate such as a glass or acrylate glazing material covered with a photocatalytic coating including crystallized particles having photocatalytic properties and a mineral binder comprising at least one oxide of a metal having photocatalytic properties. U.S. Pat. Nos. 6,569,520 and 6,881,702 disclose a photocatalytic composition and method for preventing algae growth on building materials such as roofing granules. A plurality of photocatalytic particles, such as anatase titanium dioxide, is dispersed in a silicate binder to form an exterior coating for a substrate such as a roofing granule or concrete surface. At least a portion of some of the photocatalytic particles is exposed on the surface of the coating.

There is a continuing need to prevent the appearance of undesirable algae growth on roofing shingles and other roofing materials.

SUMMARY OF THE INVENTION

In one aspect, the present invention provides biocidal roofing granules comprising a mineral core and an exterior coating covering the mineral core. The exterior coating includes at least one porous layer having a network of pores formed therein, and the porous inorganic layer contains at least one biocidal photocatalytic metal oxide in the network of pores. Preferably, the at least one porous layer is a mesoporous layer. Optionally, the exterior coating also includes at least one non-photocatalytic metal oxide, and/or at least one biocidal organic compound to limit, or to prevent, the growth of micro-organisms, in particular the growth of algae. The present invention also provides a process for preparing such biocidal roofing granules. The present invention also provides roofing products, including roofing shingles which include such biocidal roofing granules.

In another aspect, the present invention provides roofing products including a biocidal coating, such as roofing shingles. These roofing products according to the present invention comprise a base material, such as a conventional roofing shingle, and an exterior coating covering the base material. The exterior coating includes at least one porous layer having a network of pores formed therein; and the porous inorganic layer contains at least one biocidal photocatalytic metal oxide in the network. Optionally, the exterior coating also includes at least one non-photocatalytic metal oxide, and/or at least one biocidal organic compound to limit, or to prevent, the growth of microorganisms, in particular the growth of algae. The present invention also provides a process for preparing such roofing products.

Preferably, the at least one porous layer comprises an inorganic material selected from the group consisting of silica, alumina, zirconia and titania, and mixtures thereof.

It is also preferred that the porous layer have an average pore diameter of between 1 nm and 100 nm. Preferably, the at least one porous layer has a total pore volume of at least $0.5 \times 10^{-3}$ cm$^3$/g for pores having an average diameter less than 100 nm, and that the total pore volume is less than 0.1 cm$^3$/g for pores having an average diameter less than 100 nm. More preferably, the at least one porous layer has a total pore volume of between $0.7 \times 10^{-3}$ and $1 \times 10^{-2}$ cm$^3$/g for pores having an average diameter less than 76 nm. Preferably, the at least one porous layer has an average thickness no greater than about 40 µm, more preferably no greater than 20 µm, and still more preferably the at least one porous layer has an average thickness between 0.5 µm and 10 µm, and even more preferably, the at least one porous layer has an average thickness between 1 µm and 5 µm.

It is preferred that the at least one photocatalytic metal oxide be selected from the group consisting of photocatalytic titanium oxide, photocatalytic copper oxide, photocatalytic vanadium oxide, and photocatalytic zinc oxide, and mixtures thereof. Photocatalytic titanium dioxide is especially preferred. The at least one photocatalytic metal oxide can be optionally dispersed in the at least one porous layer in combination with a metal such as Pt, Au, Os, Pd, Ni, Sn, Cu, Fe, Mn, Rh, Nb, or Ru, for example, to expand the spectral sensitivity of the at least one photocatalytic metal oxide.

Preferably, the at least one photocatalytic metal oxide comprises from about 1 to 60 percent by weight of the at least one porous layer. Preferably, the at least one photocatalytic metal comprises from about 1 to 20 percent by weight of the exterior covering including the at least one porous layer.

In the biocidal granules according to the invention, the mineral core serves as a support for the porous layer, which includes the at least one photocatalytic metal oxide. The at least one photocatalytic metal oxide provides an antimicrobial or biocidal effect. In addition, the porous layer forms, to some extent, a reservoir for the at least one optional additional biocide, such as an organic biocidal compound or an inorganic biocidal compound, which can thus diffuse outwardly. In the roofing products including a biocidal coating, the porous layer provides similar functions as a carrier for the at least one photocatalytic metal oxide and as a reservoir for the optional at least one additional biocide.

Because of the antimicrobial effect of the at least one photocatalytic metal oxide, it is possible to control the growth of microorganisms reliably.

Preferably, the at least one photocatalytic metal oxide comprises from about 1 to 60 percent by weight of the at least one porous layer. Preferably, the at least one photocatalytic metal comprises from about 1 to 20 percent by weight of the exterior covering including the at least one porous layer.

The optional at least one organic or inorganic biocidal compound further increases the flexibility and usefulness of this approach, permitting the controlled release of the organic biocidal compound, so that the roofing products can be tailored to specific local conditions.

The porous layer comprises an inorganic material, preferably an oxide of a metal or a metalloid, and is more preferably selected from the group consisting of silica, alumina, zirconia and titanium oxide, and mixtures thereof. Preferably, the porous layer comprises silica.

DETAILED DESCRIPTION

Preferably, the at least one porous layer is mesoporous. By "mesoporous" is meant having an average pore diameter from about 5 nm to about 50 nm.

As used in the present specification, the strength in color space E is defined as $E=(L^2+a^2+b^2)^{1/2}$, where L, a, and b are the color measurements for a given sample using the 1976 CIE Lab color space. The total color difference $\Delta E$ is defined as $\Delta E=(\Delta L^2+\Delta a^2+\Delta b^2)$ where $\Delta L$, $\Delta a$, and $\Delta b$ are respectively the differences in L, a and b for two different color measurements.

Figure 1:
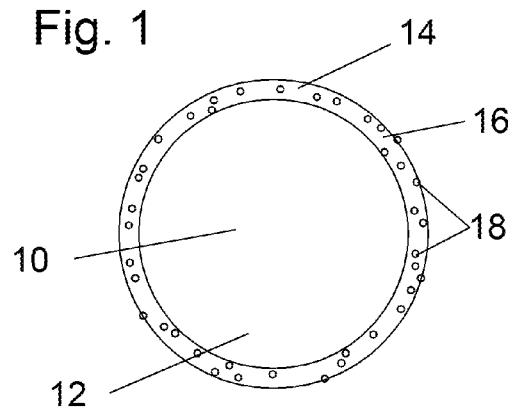
FIG. 1 is a schematic illustration of a first type of biocidal roofing granule according to the present invention.
Figure 2:
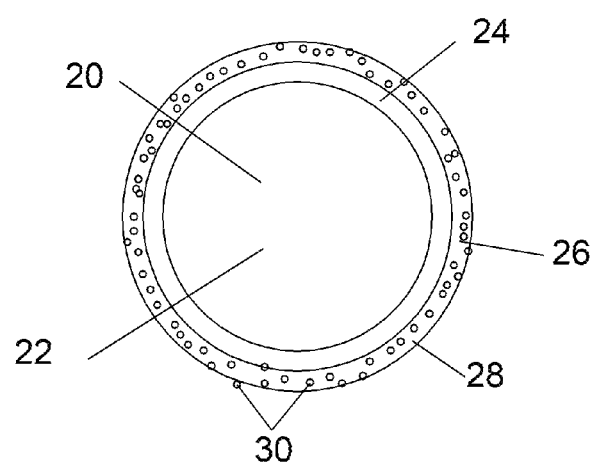
FIG. 2 is a schematic illustration of a second type of biocidal roofing granule according to the present invention.
Figure 3:
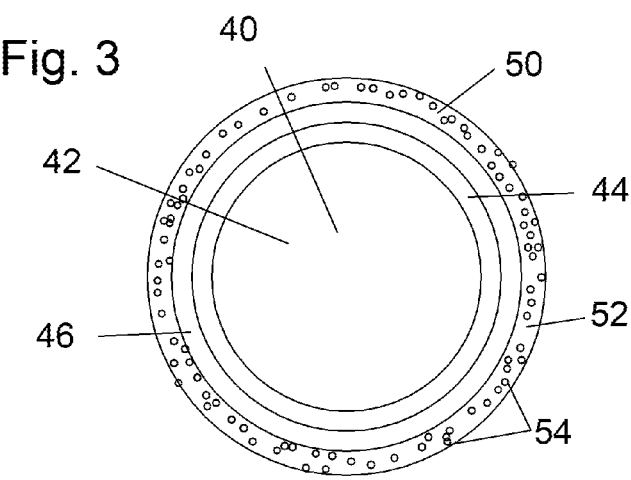
FIG. 3 is a schematic illustration of a third type of biocidal roofing granule according to the present invention.

Referring now to the drawings, in which like reference numerals refer to like elements in each of the several views, there are shown schematically in FIGS. 1-3 examples of biocidal roofing granules according to the present invention.

FIG. 1 is a schematic representation of a first type of biocidal roofing granule 10 of the present invention. FIG. 1 schematically illustrates a biocidal granule 10 including an inert mineral core particle 12 covered with a mesoporous coating layer 14 composed of an inert porous inorganic matrix 16 and at least one photocatalytic metal oxide 18 contained therein and at least partially protruding through the exterior surface of the mesoporous coating layer 14.

FIG. 2 is a schematic representation of a second type of biocidal roofing granule 20 of the present invention. FIG. 2 schematically illustrates a biocidal granule 20 including an inert mineral core particle 22 covered with a color coating layer 24, which in turn is covered with an outer mesoporous coating layer 26 composed of an inert porous inorganic matrix 28 and at least one photocatalytic metal oxide 30 contained therein and at least partially protruding through the exterior surface of the mesoporous coating layer 26.

FIG. 3 is a schematic representation of a third type of biocidal roofing granule 40 of the present invention. FIG. 3 schematically illustrates a biocidal granule 40 including an inert mineral core particle 42 covered with a color coating layer 44, which in turn is covered with an inner mesoporous coating layer 46, which in turn is covered with an outer mesoporous coating layer 50 composed of an inert porous inorganic matrix 52 and at least one photocatalytic metal oxide 54 contained therein and at least partially protruding through the exterior surface of the outer mesoporous coating layer 50. The biocidal granule 40 also includes at least one organic biocide or inorganic biocide distributed in the pore network of the inner mesoporous coating layer 46 and the outer mesoporous coating layer 50.

The mineral core can consist of any chemically inert matter, which can be used as support to the at least one porous inorganic layer, and having, moreover, mechanical properties enabling the mineral core to resist the various operations implemented during the manufacture of the asphalt shingles. For example, the mineral core can be formed from materials available in the natural state, such as talc, granite, siliceous sand, andesite, porphyry, marble, syenite, rhyolite, diabase, quartz, slate, basalt, sandstone, and marine shells, as well as material derived from recycled manufactured goods, such as bricks, concrete, and porcelain.

The mineral core can be provided as granules, generally obtained by crushing above mentioned materials and sifting of the products obtained, having a size of particle, taken in its greatest dimension, ranging between about 0.2 and 3 mm, preferably between about 0.4 mm and 2.4 mm, and more preferably about 1 mm. The mineral core can have a form approaching that of a sphere, but it can also have the shape of a plate, i.e., of a relatively planar element of little thickness compared to its surface.

Preferably, the mineral core has a low porosity, defined in particular as having an average pore volume less than about $1 \times 10^{-3}$ cm$^3$/g measured for pores having an average diameter of less than 70 nm.

Preferably, the average mass of the particles forming the mineral core generally lies between about 0.05 mg and 15 mg, and preferably between about 0.3 mg and 7 mg.

Before being covered by the at least one porous exterior inorganic layer, the mineral core can undergo one or more operations to provide a color coating, in particular by the application of one or more layers of colored coating including a binder, such as an alkali metal silicate, and one or more compounds of the color desired, for example selected among the pigments of metallic oxides and carbon black. The techniques for application of such colored layers are well-known in the roofing granule art. The colored coating layer can also include at least one non-photocatalytic metal oxide, such as copper oxide, zinc oxide, or a mixture thereof, as an optional additional biocidal material.

In addition, the mineral core can be covered with one or more intermediate coating layers between the mineral core and the at least one porous exterior inorganic layer. These intermediate coating layers can be formed from a binder, such as an alkali metal silicate binder, and at least one non-photocatalytic metal oxide, such as copper oxide, zinc oxide, or a mixture thereof, as an optional additional biocidal material. Preferably, such intermediate coating layers are provided between the mineral core and the color coating layer.

Further, the mineral core can be covered with one or more intermediate porous coating layers between the mineral core and the at least one porous exterior inorganic layer. The at least one intermediate porous coating layers can serve as a reservoir for the optional at least one organic biocide.

The biocidal granules can comprise, moreover, at least one blocking coating layer covering in whole or in part the at least one intermediate porous layer. The blocking coating layer functions to delay the diffusion of the optional organic biocide from the intermediate porous coating layer. Although the blocking coating layer is permeable to the optional organic biocide, the blocking coating layer preferably has a porosity less than that of the subjacent porous layer containing the optional organic biocide. Preferably, the porosity of the blocking coating layer is less by at least 20%, and more preferably less than 50%, than that of the intermediate coating porous layer containing optional organic biocide.

The blocking coating layer can comprise inorganic material, for example of comparable nature to that which constitutes the at least one intermediate porous layer, or in the alternative, the blocking coating layer can comprise organic material, preferably an organic polymeric material such as a polyacrylate, polyurethane, or silane-terminated polyurethane or fluoropolymer.

The outermost coating layer covering the mineral core is preferably the at least one porous layer which includes the at least one photocatalytic metal oxide. This at least one outer porous layer preferably has an average pore diameter ranging from about 1 nm to 100 nm, and more preferably between about 2 nm and 50 nm. It is especially preferred that the average pore diameter of this at least one outer porous layer be about 5 nm.

The at least one outer porous layer preferably has a total pore volume of at least about $0.5 \times 10^{-3}$ cm$^3$/g for pores less than 100 nm in average diameter, and preferably less than about 0.1 cm$^3$/g for pores less than 100 nm in average diameter. Preferably, the at least one outer porous layer has a total pore volume ranging from about $0.7 \times 10^{-3}$ cm$^3$/g to $1 \times 10^{-2}$ cm$^3$/g for pores less than about 76 nm in average diameter. More preferably, the at least one outer porous layer has a total pore volume of about $1.25 \times 10^{-3}$ cm$^3$/g for pores less than about 76 nm in average diameter.

The specific surface of the at least one outer porous layer is preferably greater than about 1 m$^2$/g, preferably, the specific surface area of the porous layer is from about 1.25 m$^2$/g to 100 m$^2$/g.

The at least one outer porous layer has an average thickness with most equal to about 20 μm, preferably ranging between 0.5 and 10 gm, advantageously between 1 and 5 μm. The outer porous layer can be made up of one or more sublayers, preferably from 1 to 3 sublayers, with each such sublayer having a thickness of from about 1 μm to 2 μm.

The optional organic biocide, which can be provided in the optional at least one intermediate porous inorganic layer, can be selected from organic compounds known to limit or prevent the development of microorganisms. For example, the at least one optional biocide can be an aldehyde, a condensate of formaldehyde, a triazine, a phenol, an ester of carbonic acid, an amide, a carbamate, a thiocarbamate, a thiocyanate, a dibenzarnidine, a derivative of pyridine, a triazole, a thiazole, an isothiazolone such as the isothiazolin-3-one, a N-haloalkylthio compounds, or a mixture of these compounds. Preferred organic biocides are isothiazolin-3-ones, in particular, 2-n-octyl-4-isothiazolin-3-one (OIT), and 4,5-dichloro-2-(n-octyl)-4-isothiazolin-3-one (DCOIT).

The amount of the optional organic biocide in the granule depends on the nature and the characteristics of intermediate inorganic porous layer(s), in particular the thickness, and the volume of pores available. In general, the quantity of biocide can be up to about 4 percent by weight of the granule, preferably up to about 2.5 percent, and more preferably up to about 1 percent. Depending on the thickness of the at least one porous layer, the biocide can also be coated outside the at least one porous layer, and the quantity of biocide can be up to about 10 percent by weight of the granule, preferably up to about 8 percent by weight of the granule.

The present invention also provides a process for preparing biocidal roofing granules. This process includes the steps of providing a mineral core, preparing a gel-forming inorganic coating medium, providing at least one biocidal photocatalytic metal oxide, coating the mineral core with the gel-forming inorganic coating medium, forming a porous coating layer on the mineral core from the sol of inorganic precursor material, the porous coating layer having a pore network; and disposing the at least one photocatalytic metal oxide in the pore network.

The gel-forming inorganic coating medium can be a gel-forming inorganic sol. Preferably, the gel-forming inorganic coating medium is a sol selected from the group consisting of silica sol-gels, colloidal silica media, colloidal zirconia media, colloidal titania media, and colloidal alumina media.

In one embodiment of the present invention, the biocidal roofing granules are prepared by treating the mineral core with a sol of inorganic precursor ready to form the porous layer. The sol includes an inorganic precursor material, a template material for forming the pore network, and the at least one photocatalytic metal oxide.

Formation of the porous inorganic material from the inorganic precursor material by the sol-gel method is well-known in the art. As is understood in the art, a "sol" is a dispersion of colloidal particles dispersed in a liquid; and by "gel" is meant a network of polymeric chains. Conventionally, the sol-gel method as applied to film formation on a target surface is understood to include the steps of forming a sol of colloidal particles of inorganic precursor material dispersed in a liquid carrier; applying the sol of colloidal particles to surface to be covered (i.e. film deposition); gelling the mixture on the surface so as to form a three-dimensional network of colloidal particles and a network of pores (i.e. a xerogel), and eliminating the liquid phase to obtain a thickening or the chemical stabilization of the network of pores and formation of a film on the surface to be covered. The physics and chemistry of the sol-gel method are reviewed in C. Jeffrey Binker et al., *Sol-Gel Science* (Academic Press, Boston 1990), incorporated herein by reference. The sol of inorganic precursor material can also include a sacrificial template material, which is removed after film formation to provide the pore network. In the absence of a template material, control of the size and extent of aggregation of the colloidal particles of inorganic precursor material during film deposition, and control of the relative rates of condensation and evaporation of the liquid carrier, determines the characteristics of the pore network so formed, including the pore volume of the coating layer, the pore size, and the surface area of the pores. Conversely, when a template material is included in the sol of inorganic precursor material, the nature and amount of the template material affects the characteristics of the pore network obtained. For example, in the present process, templated mesoporous silica films or coating layers are synthesized through a solution phase process involving the association of a surfactant or block copolymer templating material with silica precursor materials that occurs during evaporation of the solvent employed. During film formation, it is believed that a liquid crystalline structure having nanoscale periodicity is formed. This structure is subsequently solidified by condensation of the silica precursor material, and the templating material is subsequently removed to provide the pore structure, such as by calcination or extraction.

According to one presently preferred embodiment, the biocidal granules of the present invention are obtained by treating a substrate of mineral core with a sol including the inorganic precursor, then drying at a temperature ranging between 20 and 80 degrees C., preferably between 40 and 70 degrees C., and more preferably between 50 and 65 degrees C. This embodiment makes it possible to obtain in a single stage a granule with microporous coating layer, that is, a coating layer having a pore diameter ranging between about 0.5 and 2 nm, and preferably about 1 nm.

According to another presently preferred embodiment, the biocidal granules are obtained in a multiple step process, the process comprising treating the substrate or mineral core with a sol of inorganic precursor including a templating material or structuring agent to form a coating layer on the surface of the substrate, and subsequently calcining the coating layer at a sufficient temperature to eliminate the structuring agent.

In one aspect of the process of the present invention, the substrate employed is simply the mineral core, and a single mesoporous coating layer is formed on the surface of the substrate. In this case, the sol includes both the inorganic precursor material and the at least one photocatalytic metal oxide as well as a templating material. In this case the templating material can be removed by calcination at an elevated temperature. Templating materials that are removable by calcination at an elevated temperature include organic surfactants as well as organic block copolymers.

In another aspect of the process of the present invention, the substrate employed is a conventional colored roofing granule, and a single mesoporous coating layer is formed on the surface of the colored roofing granule. In this case, the sol includes both the inorganic precursor material and the at least one photocatalytic metal oxide as well as a templating material. In this case, the templating material can be removed by calcination at an elevated temperature.

Preferably, the at least one photocatalytic metal oxide is selected from the group consisting of photocatalytic titanium oxide, photocatalytic copper oxide, photocatalytic vanadium oxide, photocatalytic zinc oxide, and mixtures thereof. Photocatalytic titanium dioxide is especially preferred. The at least one photocatalytic metal oxide can be optionally dispersed in the at least one porous layer in combination with at least one additional metal such as Pt, Au, Os, Pd, Ni, Sn, Cu, Fe, Mn, Rh, Nb, or Ru, for example, to expand the spectral sensitivity of the at least one photocatalytic metal oxide. Doping the photocatalytic metal oxide with the at least one additional metal can alter the spectral sensitivity of the photocatalytic metal oxide so that the photocatalytic effect can take place even in the presence of lower energy electromagnetic radiation, such as portions of the visible spectrum.

In yet another aspect of the process of the present invention, the substrate employed is an algae-resistant roofing granule, and a single mesoporous coating layer is formed on the surface of the algae-resistant roofing granule. Algae-resistant roofing granules typically include at least one non-photocatalytic algaecidal metal oxide, preferably copper oxide and/or zinc oxide, in at least one coating layer on their mineral cores. Algae-resistant roofing granules are disclosed, for example, in U.S. Pat. Nos. 3,507,676, 4,092,441, 5,356,664, 6,124,466, each incorporated herein by reference. In this case, the sol includes both the inorganic precursor material and the at least one photocatalytic metal oxide, as well as a templating material. In this case, the templating material can be removed by calcination at an elevated temperature.

In another aspect of the process of the present invention, the substrate employed, which can be a mineral core, a conventional colored roofing granule, or an algae-resistant roofing granule, is covered with a sodium ion barrier layer prior to application of the single mesoporous coating layer to the surface of the substrate. As is known in the art, sodium ions tend to interfere with or "poison" the beneficial photocatalytic action of the at least one photocatalytic metal oxide. The preparation and deposition of sodium ion barrier coating is disclosed, for example, in U.S. Pat. Nos. 6,362,121 and 6,465,088, each incorporated herein by reference.

In still another aspect of the process of the present invention, the substrate employed, which can be a mineral core, a conventional colored roofing granule, or an algae-resistant roofing granule, or a substrate including a sodium ion barrier layer, is first coated with one or more initial or inner mesoporous coating layers, which may optionally include the at least one photocatalytic metal oxide. Preferably, however, in this aspect of the process of the present invention, the one or more inner mesoporous layers does not include the at least one photocatalytic metal oxide, and is instead provided to increase the ultimate thickness of the mesoporous network on the exterior of the substrate. In this case, the sol includes both the inorganic precursor material and the at least one photocatalytic metal oxide as well as a templating material. In this case, the templating material can be removed by calcination at an elevated temperature. In this case, an optional organic biocide can be introduced into the porous network subsequent to formation of the pore network. Since it is preferred that the at least one photocatalytic metal oxide be present in the outermost layer of the biocidal particles, this aspect of the process of the present invention provides for a porous network to serve as a reservoir for the optional organic biocide, while reducing the proportion of the at least one photocatalytic metal oxide present in the interior of the porous network, and thus making more efficient use of the at least one photocatalytic metal oxide.

In another aspect of the present invention, the substrate comprises a roofing material, such as the upper or outer surface of a roofing shingle surfaced with roofing granules, such as conventional colored roofing granules, algae-resistant roofing granules, or a mixture thereof, or such a roofing material covered with an optional initial or inner mesoporous layer, and an outer mesoporous coating layer is formed on the substrate. In this case, the sol for producing the outer mesoporous coating includes both the inorganic precursor material and the at least one photocatalytic metal oxide as well as a templating material. In this case the templating material cannot be removed by calcination at an elevated temperature, because the roofing material typically includes bituminous material which could be degraded, damaged or destroyed by exposure to temperatures sufficient to calcine the templating material. In this case, the templating material is preferably selected so that the templating material can be removed by an alternative method. For example, a surfactant material that is removable from the porous network by an extraction method can be chosen as the templating material. In the alternative, the templating material can be a templating material that is photocatalytically degradable, and is photocatalytically degraded by the at least one photocatalytic metal oxide, such as titanium dioxide, embedded in the at least one porous inorganic layer.

By structuring agent (or template), is understood an organic material promoting the creation of pores in the inorganic matter network. This organic material can be broken up by calcination at a temperature greater than about 200 degrees C., and preferably less than about 1000 degrees C., advantageously ranging between about 400 degrees C. and 700 degrees C., and more preferably at about 450 degrees C.

Example of structuring agents or templating materials include organic polymers such as copolymers, such as poly(alkyleneoxide) block copolymers, and in particular, poly(oxyethylene)-(oxypropylene)-(oxyethylene) triblock copolymers, and quaternary ammonium salts such as cetyltrimethylammonium bromide.

Examples of block copolymer structuring agents are amphiphilic poly(alkylene oxide) block copolymers include triblock copolymer in which relatively hydrophilic blocks, such as linear poly(oxyethylene) blocks extend from either end of a central linear hydrophobic block, such as a poly(oxypropylene) block or a poly(oxybutylene) block. Preferably, the hydrophilic blocks have a degree of polymerization of at least 5 and the central hydrophobic block has a degree of polymerization of at least 30. The use of triblock copolymers as templating agents is discussed, for example, in D. Zhao et al., *Science*, 279 (1998) 548-552, incorporated herein by reference.

Examples of surfactant structuring agents include cetylpyridinium chloride, cetylpyridinium bromide, cetyltrimethylammonium chloride, cetyltrimethylammonium bromide, cetyldimethylethylammonium bromide, stearyltrimethylammonium chloride, stearyltrimethylammonium bromide, myristyltrimethylammonium chloride, myristyltrimethylammonium bromide, lauryltrimethylammonium chloride, lauryltrimethylammonium bromide, decylltrimethylammonium chloride, decyltrimethylammonium bromide, and mixtures thereof.

The proportion of the structuring agent or templating material employed depends on the desired degree of porosity and the desired pore size. In general, the structuring agent comprises from about 20 to 80% of the weight of the inorganic precursor, and preferably 40 to 70% of the weight of the inorganic precursor.

When an optional organic biocide is to be introduced into the porous network, the selection of the structuring agent used to form the porous network should be determined taking into consideration the size of optional organic biocide molecule to be introduced into the pores. Preferably, the size of the pores is greater then the size of the optional organic biocide molecule.

The process of the present invention makes it possible to obtain a mesoporous layer of porosity containing pores having an average diameter ranging between about 2 and 50 nm, and preferably having an average diameter of less than 10 nm.

In a first alternative, the optional organic biocide is applied in the form of a solution to the exterior porous inorganic layer. Preferably, the solution includes both the optional organic biocide and a volatile solvent, preferably a volatile organic solvent. The volatile solvent is removed after application of the solution to the porous layer, for example by evaporation according to any known method. Examples of volatile organic solvents that can be employed include alkanes, in particular cyclohexane, alcohols, in particular ethanol, ketones, in particular acetone, and chlorinated compounds, in particular methylene chloride. Water-based organic solvent azeotropes with suppressed boiling points can also be employed. The biocide solution can be applied by spraying, or by immersing the substrate, including the porous layer, in the solution including the optional organic biocide.

In a second alternative, the optional organic biocide is included in a sol containing the inorganic precursor, which can be the same or different from that which is used to obtain the porous inorganic layer on the substrate. Preferably, the substrate including the porous inorganic layer is immersed in the sol including the optional organic biocide, and the solvent is subsequently removed by drying.

When a sol is employed in the process of the present invention, the sol can be prepared in any manner known in the art sufficient to provide a gel-forming sol material that can be further processed into a mesoporous inorganic coating. For example, the sol can be a silica sol prepared by an ion exchange technique, such as by passing sodium silicate through a proton-exchanging ion-exchange column, a silica sol prepared by an organic reaction technique, such as by mixing tetraethoxysilane and ethanol followed by the addition of base, by an inorganic reaction technique, such as by mixing solutions of ammonium chloride and sodium silicate, followed by removal of the electrolyte and redispersion of the sol, and the like.

When a sol is employed in the process of the present invention, the sol is preferably an aqueous suspension prepared from one or more organic precursors selected from alkylsilanes, and alkoxysilanes, including tetralkoxysilanes such as tetramethoxysilane (TMOS), tetraethoxysilane (TEOS), tetra-n-propoxysilane, tetra-n-butaoxysilane, and tetrakis(2-methoxyethoxy)silane; organotrialkoxysilanes such as methyltriethoxysilane (MTEOS), methyltrimethoxysilane, methyl tri-n-propoxysilane, phenyl triethoxysilane, and vinyl triethoxysilane, siloxane oligomers such as hexamethoxydisiloxane, and octamethoxytrisiloxane; aluminum alkoxides such as aluminum tributoxide, titanium alkoxides such as titanium tetraethoxide and titanium tetraisopropoxide, zirconium alkoxides such as zirconium tetraethoxide, aluminum chloride, zirconyl chloride, and the like. Conventionally, the sol is treated with acid, preferably at a temperature ranging between about 20 and 100 degrees C. and in the presence of an alcohol such as ethanol, for sufficient length of time to obtain the conversion of the inorganic precursor into corresponding metallic oxide.

In the alternative, when a sol is employed in the present invention, the sol can be prepared by dispersing a pyrogenic material in a suitable liquid medium. Examples of pyrogenic materials include pyrogenic silica made by flame oxidation such as those available under the Aerosil and Cab-O-Sil trademarks, pyrogenic titania, pyrogenic alumina, pyrogenic zirconia, and mixtures thereof. By "pyrogenic material" is meant a material generated during a high energy process, such as in a furnace at an elevated temperature, in a flame, in a laser beam, in a particle beam such as an electron beam, in a plasma, or the like. Examples of suitable liquid media include water and other polar solvents. In addition, the sol can be prepared from a combination of one or more pyrogenic materials and at least one organic precursor, such as alkylsilanes, and alkoxysilanes, including tetralkoxysilanes such as tetramethoxysilane (TMOS), tetraethoxysilane (TEOS), tetra-n-propoxysilane, tetra-n-butaoxysilane, and tetrakis(2-methoxyethoxy)silane; organotrialkoxysilanes such as methyltriethoxysilane (MTEOS), methyltrimethoxysilane, methyl tri-n-propoxysilane, phenyl triethoxysilane, and vinyl triethoxysilane, siloxane oligomers such as hexamethoxydisiloxane, and octamethoxytrisiloxane; aluminum alkoxides such as aluminum tributoxide, titanium alkoxides such as titanium tetraethoxide and titanium tetraisopropoxide, zirconium alkoxides such as zirconium tetraethoxide, aluminum chloride, zirconyl chloride, and the like.

In another aspect, the present invention provides biocidal mesoporous polymeric coatings. The preparation of mesoporous polymeric coating materials is disclosed, for example, in U.S. Pat. No. 6,537,703, incorporated herein by reference.

In the alternative, powder coating materials can be employed to provide a porous exterior coating on the roofing granules or roofing products, or as a base coating for a mesoporous coating layer including at least one biocide. Powder coating materials are typically dry, solid powder materials that include a polymeric resinous binder with a melting temperature above ambient temperature and optional pigments, extenders, flow control agents, and/or other additives. Powder coating materials or compositions for use in the present invention preferably include both a polymeric binder and at least one biocidal material.

Suitable powder coating material should have excellent outdoor durability; a melting temperature for application of between 66 degrees C.-204 degrees C. (150 degrees F.-400 degrees F.); and low viscosity upon melting to completely impregnate the tie-layer in a relatively short period of time. By "low viscosity" is meant a viscosity of from about 50 centipoise to 3,000 centipoise.

Examples of suitable powder coating compositions include thermoplastic and thermoset powder coating compositions. Thermoplastic powder coating compositions are frequently employed to provide coating of at least about 250 microns. Thermosetting powder coating compositions are frequently employed to provide thinner coatings, such as coatings with a thickness of from about 20 to 80 microns. Suitable powder coating polymeric materials include, but are not limited to, acrylic and related copolymers, polyesters, polyamides, epoxies, polyolefin and its alloys, polypropylene, acid containing polyolefins such as polyethylene acrylic acid or polyethylene methacrylic acid, polyvinyl chloride, polyester block amide, ethylene chlorotrifluoroethylene, or polyvinylidene fluoride. Examples of thermosetting materials include epoxy, polyester, and acrylic thermosetting materials. Examples of thermoplastic materials include polyamide, polyethylene, polypropylene, polyvinyl chloride, polyester, and polyvinylidene fluoride thermoplastic materials.

Preferably, a powder coating composition having good exterior durability and weatherability characteristics is employed. Examples of powder coating compositions providing coatings with good exterior durability include thermoplastic polyester compositions, thermoplastic polyvinylidene fluoride compositions, thermosetting polyester compositions such as hydroxyalkylamide polyesters, thermosetting epoxy resin compositions, thermosetting epoxy-polyester hybrid coating compositions, thermosetting polyester-triglycydyl isocyanurate compositions, thermosetting GMA acrylic compositions, thermosetting acrylic urethane compositions, and thermosetting polyester urethane compositions.

Powder coating compositions for use in the present invention are preferably provided with at least one biocidal material. In addition, powder coating compositions for use in the preparative process of the present invention can include other components, such as curing agents or hardeners, extenders, and additives such as thixotropes, flow modifiers, and the like.

The biocidal granules of the invention can be used to control the development of microorganisms in particular of algae in roofing material, to limit the appearance of unappealing blotches and spots on the roofing materials. The roofing material can be an organic asphalt shingle, containing fibers of wood or cellulose, or a glass fiber reinforced shingle or roofing membrane.

The coating compositions used in preparing the biocidal granules can include other components, such as conventional metal oxide colorants of the type employed in the manufacture of roofing granules, solar heat-reflective pigments such as titanium dioxide, other biocidal materials, and the like.

The biocidal granules prepared according to the process of the present invention can be employed in the manufacture of biocidal roofing products, such as biocidal asphalt shingles, using conventional roofing production processes. Typically, bituminous roofing products are sheet goods that include a non-woven base or scrim formed of a fibrous material, such as a glass fiber scrim. Bituminous roofing products are typically manufactured in continuous processes in which a continuous substrate sheet of a fibrous material such as a continuous felt sheet or glass fiber mat is immersed in a bath of hot, fluid bituminous coating material so that the bituminous material saturates the substrate sheet and coats at least one side of the substrate. Thus, the substrate is coated with one or more layers of a bituminous material such as asphalt to provide water and weather resistance to the roofing product. The reverse side of the substrate sheet can be coated with an anti-stick material such as a suitable mineral powder or a fine sand. The upper side of the roofing product is typically coated with mineral granules to provide durability, reflect heat and solar radiation, and to protect the bituminous binder from environmental degradation. The roofing granules are typically distributed over selected portions of the upper side of the substrate, and the bituminous material serves as an adhesive to bind the roofing granules to the sheet when the bituminous material has cooled.

The biocidal granules of the present invention can be mixed with conventional roofing granules, and the granule mixture can be embedded in the surface of such bituminous roofing products using conventional methods. The biocide granules can be mixed with untreated granules to comprise about 10 percent by weight of the total granule weight, and preferably, less than 10 percent by weight.

Alternatively, biocidal granules of the present invention can be substituted for conventional roofing granules in the manufacture of bituminous roofing products to provide those roofing products with resistance to biological discoloration and degradation. One or more classes of the biocidal granules can be applied sequentially to the roofing product surface, followed by application of conventional roofing granules. In one embodiment of the process of the present invention, a first class of biocidal granules is first applied to the surface of the roofing product, followed by application of a second class of biocidal granules, followed finally by application of conventional roofing granules. In another embodiment, one or more classes of the biocidal granules can be pre-mixed and applied simultaneously to the surface of the roofing product. In another embodiment of the present invention, a mixture of two or more classes of biocidal granules is first applied to the surface of the roofing product, followed by application of conventional roofing granules. Given the order of application, any excess granules that are not successfully embedded in the surface of the roofing product are likely to be conventional granules. Thus, the order of application of these embodiments of the process of the present invention is likely to permit more precise loading of the roofing product surface with the classes of biocidal granules than otherwise. In another embodiment of the present invention, biocidal granules may be employed to cover a substantial portion of, or substantially all of the roofing product surface, or of the exposed portion of the roofing product surface.

The roofing product sheet can be cut into conventional shingle sizes and shapes (such as one foot by three feet rectangles), slots can be cut in the shingles to provide a plurality of "tabs" for ease of installation and aesthetic effects, additional bituminous adhesive can be applied in strategic locations and covered with release paper to provide for securing successive courses of shingles during roof installation, and the finished shingles can be packaged. More complex methods of shingle construction can also be employed, such as building up multiple layers of sheets in selected portions of the shingle to provide an enhanced visual appearance, or to simulate other types of roofing products. Release strips can also be strategically applied to the shingles so as to line up with sealing adhesive so that stacked shingles can be packaged without the need for separate release paper covers for the additional adhesive. It will be noted that the roofing product sheet can also be retained in substantially larger format sizes such as, for example 3 feet by 30 feet or more for membrane or roll roofing product applications.

The bituminous material used in manufacturing roofing products according to the present invention is derived from a petroleum processing by-product such as pitch, "straight-run" bitumen, or "blown" bitumen. The bituminous material can be modified with extender materials such as oils, petroleum extracts, and/or petroleum residues. The bituminous material can include various modifying ingredients such as polymeric materials, such as SBS (styrene-butadiene-styrene) block copolymers, resins, oils, flame-retardant materials, oils, stabilizing materials, anti-static compounds, and the like. Preferably, the total amount by weight of such modifying ingredients is not more than about 15 percent of the total weight of the bituminous material. The bituminous material can also include amorphous polyolefins, up to about 25 percent by weight. Examples of suitable amorphous polyolefins include atactic polypropylene, ethylene-propylene rubber, etc. Preferably, the amorphous polyolefins employed have a softening point of from about 130 degrees C. to about 160 degrees C. The bituminous composition can also include a suitable filler, such as calcium carbonate, talc, carbon black, stone dust, or fly ash, preferably in an amount from about 10 percent to about 70 percent by weight of the bituminous composite material.

In asphalt shingles, the mass of roofing granules per unit of area generally lies between 0.5 and 2.5 kg/m$^2$, preferably between 1 and 2 kg/m$^2$.

The examples which follow make it possible to illustrate the invention without, however, limiting it.

Example 1 a) Preparation of the Granules

Base granules having the following characteristics are employed:

White colored roofing granules (Product No. 93, commercially available from CertainTeed Corporation) having a white color coating (2.7% by weight titanium oxide) are used as the base granules with an average diameter of 1 mm, an average mass of 1.26 mg, a specific surface BET of 0.37 m$^2$/g, and a total pore volume (diameter<69 nm) of 6.07×10$^{-4}$ cm$^3$/g.

A sol is prepared using 22.3 ml of tetraethoxysilane (TEOS from Aldrich-Sigma, 99%); 22.1 ml of an ethanolic solution of 10% v/v of 2-n-octyl-4-isothiazolin-3-one (OIT: 0.2 M); and 9 ml of hydrochloric acid, to give a pH of 1.25. The sol is subjected to hydrolysis at 60 degrees C. for 1 hour.

50 g of base granules are immersed in the sol for 15 minutes. The resulting suspension is filtered, the granules are washed with water, and dried at 60 degrees C. for 2 hours. The resulting biocidal granules included 0.7% by weight OIT (as determined by thermogravimetry).

b) Preparation of Roofing Material

A test sample of roofing material is prepare by depositing on an aluminum plate (L=10 cm; 1=3.75 cm) a plaque prepared from a mixture of asphalt (32% in weight) and calcium carbonate (68% in weight) about the same size as the aluminum plate and having a thickness of 1.6 mm. The test sample is heated at 150 degrees C., a granule mixture is distributed on asphalt (1.61 kg/m$^2$), and partially embedded in the asphalt using a roller with a 14 cm diameter (3 passes). The granule mixture includes untreated granules (90% in weight), and biocidal granules prepared as described in a) above (10% in weight).

c) Biocidal Activity

The biocidal activity of the biocidal granules is measured as follows:

*Gloeocapsa* sp. (UTEX LB 795) is cultivated in flasks of 1 liter containing 500 ml of Allen medium, under constant ventilation, at 22 degrees C., under fluorescent light (340-380 nm). The culture is agitated (50-70 RPM; 5 to 10 minutes) at regular intervals (3 or 4 days). After twenty days of culture, the medium contains about 1×10$^6$ spores/ml.

The medium containing the spores is atomized on samples of test sample, on the face containing the granules at a distance of approximately 4 cm. Each sample is placed in a Petri dish (relative moisture higher than 80%) laid out in a drying oven at 22 degrees C. under the above mentioned conditions of illumination. The samples receive a quantity of sufficient Allen medium daily to ensure the survival of the algae.

Counting of living cells is carried out via fluorescence microscopy (enlargement×200). Ten measurements distributed on the whole of the surface of the sample are taken. From these measurements, the rate of survival=(number of alive cells at time T/number of alive cells to T=0)×100 is calculated. The results appear in the Table 1, which indicates the rate of survival of the cells for various times of incubation in the presence of biocidal granules according to the invention (Example 1) and of untreated granules (control).

Example 2

The process of Example 1 is repeated with the following modifications as follows.

Preparation of the Granules

A sol containing 17.8 g of methyltriethoxysilane (MTEOS, Aldrich-Sigma), 5.4 g of hydrochloric acid (pH 2.5) and 13.8 g of ethanol is prepared. The hydrolysis of the sol is carried out at ambient temperature (25 degree C.) over two hours.

10 ml of sol and 20 ml of an ethanolic solution containing 1.864 g of polyether triblock (ethylene oxide) 73-(propylene oxide) 28-(ethylene oxide) 73 (Pluronic PE6800 marketed by BASF) are mixed to provide a coating material.

50 g of the untreated granules of Example 1 are plunged into the coating mixture for 15 minutes. The resulting suspension is filtered and the granules are calcined in a furnace under the following conditions:

To calcine the granules, the temperature is elevated from 25 degrees C. to 100 degrees C. over a 30-minute period, and maintained at 100 degrees C. for 2 hours. The temperature is then elevated from 100 degrees C. to 150 degrees C. over a 15-minute period, and maintained at 150 degrees C. during 2 hours. The temperature is then raised from 150 degrees C. to 175 degrees C. over a 15-minute period and maintained at 175 degrees C. for 2 hours. The temperature is then raised from 175 degrees C. to 200 degrees C. over a 10-minute period, and then raised from 200 degrees C. to 300 degrees C. over a 300-minute period, and maintained at 300 degrees C. for 1 hour. The temperature is then raised from 300 degrees C. to 450 degrees C. over a 150-minute period, and maintained at 450 degrees C. for 1 hour.

The cooled calcined granules are submerged in the sol of Example 1 and are treated under the same conditions.

The granules show the following characteristics—
surface BET: 1.66 m$^2$/g
total volume of pores (diameter<76 nm): 1.25×10$^{-3}$ cm$^3$/g
thickness of the porous layer: 2 μm
content of OIT (measured by thermogravimetry): 0.7% in weight.

The results of measurements of the biocidal activity appear in Table 1.

Example 3

Example 2 is repeated except that the amount of OIT is increased to 0.4% by weight. The results of measurements of the biocidal activity appear in Table 1.

Example 4

Granules are prepared as in Example 2. After calcination and cooling, the granules are submerged in a solution of OIT with 10% v/v in cyclohexane for 4 days at the ambient temperature (20-25 degrees C.). The resulting mixture is filtered and the resulting biocidal granules are washed with cyclohexane and then dried at 60 degrees C. for 2 hours. The dried granules contain 2.52% in weight of OIT.

TABLE 1

| | Rate of survival (%) | | | |
|---|---|---|---|---|
| | T = 5 days | T = 8 days | T = 14 days | T = 19 days |
| Ex. 1 | 2.17 | 0 | 0 | 0 |
| Ex. 2 | 0.8 | 0 | 0 | 0 |
| Ex. 3 | 6.46 | 0 | 0 | 0 |
| Control | 51.11 | 34.22 | 27.11 | 31.55 |
| Reference | 4.91 | 0 | 0 | 0 |

The granules of the Examples 1 to 3 prepared according to the process of the present invention exhibit a biocide activity shown by a rate of algae survival which is less than for the control not containing a biocide. The rate of survival of the algae is strongly reduced after 5 days and is vanished after 8 days of incubation.

This survival rate is comparable to that obtained by using a mixture of granulated particles containing 10% of copper oxide loaded granules (Algae Block™ Copper Roofing Granules marketed by 3M) ("Reference" in Table 1).

Example 5

Granules are prepared as follows:

A sol A containing 10 g of tetraethoxysilane (TEOS, Aldrich-Sigma), 4.3 g of hydrochloric acid (pH 2.5) and 8.34 g of ethanol is prepared. The hydrolysis of the sol is carried out at 60 degrees C. for 1 hour.

A solution B of 3.85 g of 3.85 g of polyether triblock (ethylene oxide) 73-(propylene oxide) 28-(ethylene oxide) 73 (Pluronic PE or EP 6800, BASF) in 40.29 g of ethanol is prepared.

The solution A is added to solution B, followed by addition of 33.33 g of 15% aqueous dispersion of titanium oxide nanoparticles (S5-300A from Millennium, used as received)

50 g of the untreated granules of Example 1 are plunged into the coating mixture for 15 minutes. The resulting suspension is filtered and the coated granules are calcined in a furnace under the following conditions:

To calcine the granules, the temperature is elevated from 25 degrees C. to 100 degrees C. over a 30-minute period, and maintained at 100° C. for 2 hours. The temperature is then elevated from 100 degrees C. to 150 degrees C. over a 15-minute period, and maintained at 150 degrees C. during 2 hours. The temperature is then raised from 150 degrees C. to 175 degrees C. over a 15-minute period and maintained at 175° C. for 2 hours. The temperature is then raised from 175 degrees C. to 200 degrees C. over a 10-minute period, and then raised from 200 degrees C. to 300 degrees C. over a 300-minute period, and maintained at 300 degrees C. for 1 hour. The temperature is then raised from 300 degrees C. to 450 degrees C. over a 150-minute period, and maintained at 450 degrees C. for 1 hour.

Example 6

The process of Example 5 was repeated, except that roofing granules having a white colored coating (Product No. 93, commercially available from CertainTeed Corporation) were substituted for the uncoated roofing granules of Example 5. The white granules included a rhyolite mineral as the base material coated with an exterior white color coating including pigment grade rutile titanium oxide as a pigment and a binder comprising sodium silicate and clay.

Comparative Example 1

The process of Example 5 was repeated, except that the titanium dioxide was omitted, to provide natural granules having a mesoporous coating layer on their surface.

In order to confirm and quantify the mesoporous surface layer on the roofing granules, the pore surface area was measured using a BET apparatus. The results of the measurements are provided in Table 2 below, and confirm the presence of the mesoporous layer on the granules, in that the specific surface area of the granules with the mesoporous layer is five to ten times greater than that of the control.

TABLE 2

| Granules | Specific surface area ($m^2/g$) | Pore specific volume ($cm^3/g$) | Total adsorbed volume ($cm^3/g$) (B.J.H., C = 0.75) |
|---|---|---|---|
| Natural granules | 0.37 | $6 \times 10^{-4}$ | — |
| Example 5 | 2.13 | $6 \times 10^{-3}$ | 10.0 |
| Example 6 | 1.70 | $3.6 \times 10^{-3}$ | 4.9 |
| Comparative Ex. 1 | 1.66 | $1.2 \times 10^{-3}$ | — |

Figure 4:
FIG. 4 is a photograph showing a comparison of the photocatalytic effect of biocidal roofing granules according to the present invention with control granules.

In order to test the photocatalytic effect of the added photocatalytic metal oxide, a qualitative test was carried out by studying the photocatalytic degradation of the organic red dye rhodamine 6G under ultraviolet light. A solution of 0.04 g/l of rhodamine in water was sprayed on the granules of Example 5, Comparative Example 1, and a control consisting of natural granules, and dried. The samples were then exposed to ultraviolet light for one hour, and the resulting granules were photographed as shown in the grayscale image of FIG. 4. The granules in the upper portion of the photograph were coated with a photocatalytic coating according to the present invention (Example 5), sprayed with the rhodamine solution and exposed to ultraviolet light. The granules have natural grey color, visible in the original color photograph. The granules in the lower left portion of the photograph were coated with a photocatalytic coating and sprayed with the rhodamine solution, but were not exposed to ultraviolet light. These granules have a pronounced pink color, visible in the original color photograph from which the grayscale image was derived. The granules in the lower right portion of the photograph were sprayed with rhodamine solution and exposed to ultraviolet light. These granules also have a pronounced pink color, visible in the original color photograph. These results show that the photocatalytic coating was effective in photodegrading the rhodamine dye applied, while in the absence of the photocatalyst the control showed no degradation qualitatively. This is a qualitative test to visualize the photocatalytic activity of granules treated with titanium dioxide. This test could otherwise become quantitative if the same volume of rhodamine solution and same weight of granules were used. The difference in the intensity of the pink color between the samples can be measured from such photographs. Another qualitative method is described in Example 7.

Example 7

A conventional roofing shingle (commercially available from CertainTeed Corporation), having roofing granules partially embedded in the upper asphalt surface, was immersed in an ultrasonic bath filled with water and cleaned ultrasonically for 15 minutes. The water was replaced with ethanol, and the shingle was cleaned ultrasonically in ethanol for another 15 minutes. The shingle was then dried for 20 minutes at 80 degrees C.

ene oxide template material provides somewhat better access of the rhodamine to the photocatalytic metal oxide, in that the rhodamine is degraded somewhat more rapidly in the PE 6800-templated mesoporous coating.

TABLE 3

| Template | | Time (min) | | | | | | | | | |
|---|---|---|---|---|---|---|---|---|---|---|---|
| | | 0 | 18 | 30 | 45 | 60 | 90 | 120 | 180 | 270 | 370 |
| CTAB | ΔE | 20.05 | 9.83 | 8.32 | 6.91 | 5.61 | 4.31 | 3.81 | 2.56 | 1.13 | 0.71 |
| | Percent degradation | 0.00 | 50.97 | 58.50 | 65.54 | 72.02 | 78.50 | 81.00 | 87.23 | 94.36 | 96.46 |
| PE6800 | ΔE | 27.40 | 17.28 | 11.29 | 7.73 | 5.66 | 3.89 | 3.54 | 3.00 | 1.95 | 1.66 |
| | Percent degradation | 0.00 | 36.93 | 58.80 | 71.79 | 79.34 | 85.80 | 87.08 | 89.05 | 92.88 | 93.94 |

A solution "A" of 9.9 g of tetraethoxysilane (0.0475 M), 8.34 g of ethanol, and 4.29 g (0.238 M) of water are stirred for one hour at 60 degrees C., until the mixture becomes transparent.

A solution "B" of 3.85 g of cetyltrimethylammonium bromide (CTAB, Aldrich) in 40.29 g of ethanol is prepared.

Solution "A" is added to solution "B", followed by the addition of 22.33 g of a 15 percent by weight aqueous suspension of titanium dioxide nanoparticles (S5 300A, Millennium Chemicals, used as received), to provide a coating sol having a molar ratio of titanium to silicon of 1.32 and a CTAB to silicon molar ratio of 0.2.

The roofing shingles are immersed in the coating sol for 15 minutes, and subsequently dried at 80 degrees C. for two hours to eliminate residual ethanol.

Figure 5:
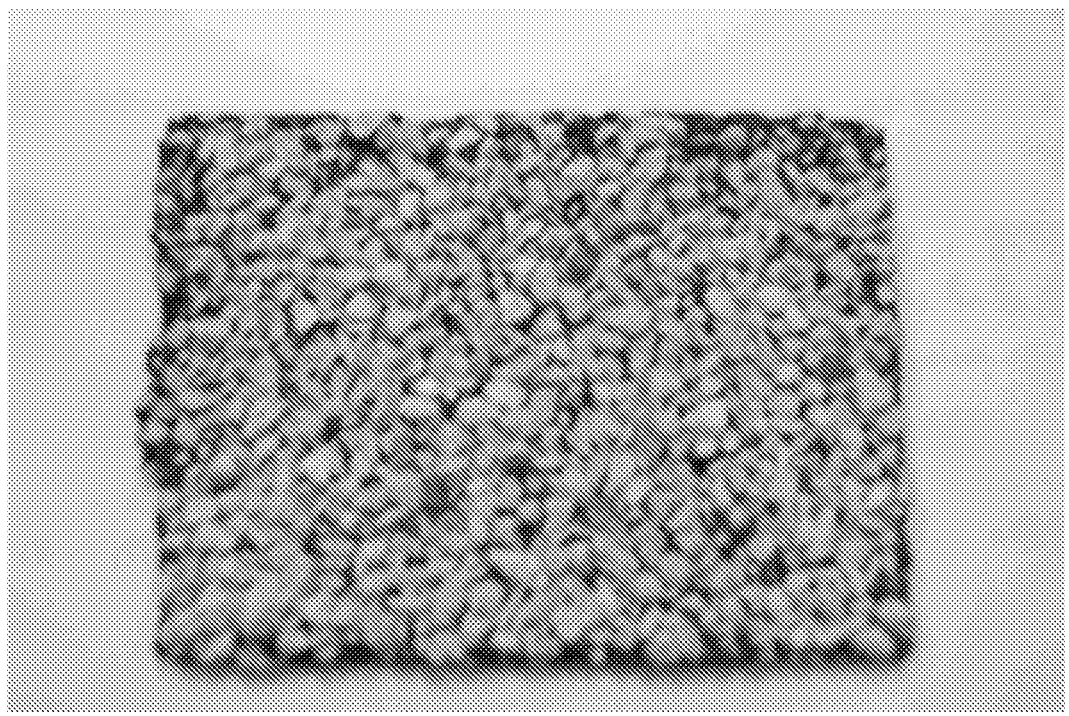
FIG. 5 is a photograph of roofing shingle of the present invention illustrating the photocatalytic activity of a mesoporous coating on the shingle.

To test for the presence of photocatalytic metal oxide in a mesoporous coating, the resulting coated shingle was sprayed with a solution of 0.04 g/l rhodamine in water. Half the shingle was then exposed to ultraviolet radiation from a mercury lamp (50 W/m$^2$ measured with monochromatic sensor at 365 nm) for 10 minutes. A photograph of the shingle is reproduced in FIG. 5. The left side of the shingle in FIG. 5 was exposed to ultraviolet radiation, and the appearance of the left side of the shingle in the original color photograph shows that the rhodamine dye has been degraded, while the right side was not exposed, and the right side of the shingle appears pink in color in the original color photograph.

The ultraviolet radiation from the mercury lamp employed corresponds to an average global power integrated over the UV-A range (315-400 nm) of 50 W/m$^2$. By comparison, exterior UV-A radiation in cloudy weather is about 30 W/m$^2$ and sunny summer weather provides about 60 W/m$^2$ of UV-A radiation.

Figure 6:
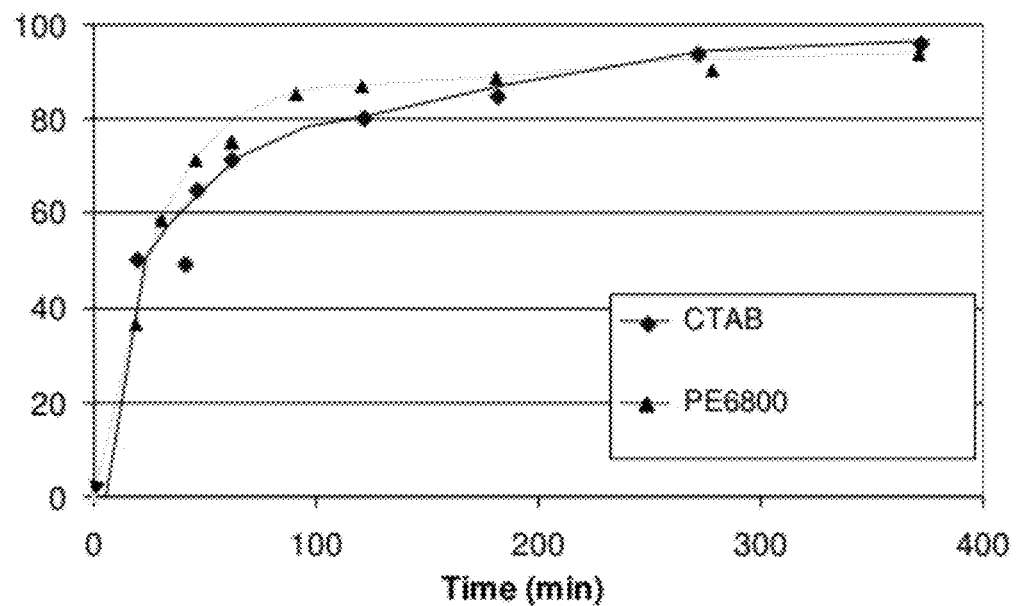
FIG. 6 is a graph showing the photocatalytic effect of two embodiments of roofing granules according to the present invention.

To test for the effectiveness of the photocatalytic metal oxide in either of the mesoporous coatings, the resulting coated shingles were sprayed with a solution of 0.04 g/l rhodamine in water. Half of each of the shingles was then exposed to ultraviolet radiation from a mercury lamp (50 W/m$^2$ measured with monochromatic sensor at 365 nm) for up to 370 minutes. The change in E as measured for rhodamine treated shingles versus shingles that had not been sprayed with the rhodamine solution is reported as a function of time of exposure in Table 3, as is the calculated percentage degradation of the rhodamine, for CTAB-templated mesoporous coating, as well as for PE 6800-templated mesoporous coating. The percent degradation of the rhodamine is plotted as a function of time in FIG. 6. The results suggest that pore structure created by the polyethyl- Example 8

Typically a mesoporous layer can be obtained on roofing granules by a sol-gel process using surfactant PE 6800 or CTAB to create an ordered porosity in the layer. Both PE 6800 and CTAB are soluble in aqueous alcohol solution. After thermal treatment at 400 degrees C., the porous layer obtained typically has a specific surface area in the range of 1.7 m$^2$/g to 3 m$^2$/g. In order to eliminate the use of alcohol or other organic solvents, a porous layer is formed from colloidal silica and polyvinyl alcohol (Mw=10$^4$–10$^5$ g/mole) as follows:

A solution of tetraethoxysilane (5 ml, TEOS 99%, Aldrich) in aqueous 0.1 M hydrochloric acid (35 ml) is prepared at 60 degrees C., and 3.3 ml of ammonium hydroxide (1M) is added to yield colloidal silica. After one hour of stirring to promote maturation of the colloidal silica, 6 g of a suspension of titanium dioxide nanoparticles (30 wt %, 2730×, Degussa) is added to the colloidal silica, followed by addition of 38 ml of an aqueous dispersion of polyvinyl alcohol (20,000 g/mole, 5.5 wt % solution). Roofing granules are then immersed in the resulting sol and dried, or the sol is spray directly on roofing shingles. Roofing granules coated with the sol are then dried at 80 degrees C. for 24 hours and subsequently calcined at 450 degrees C. for one hour. The roofing shingles coated with the sol are subsequently dried at 80 degrees C. for 24 hours. The polyvinyl alcohol serves to increase the layer thickness of the mesoporous coating, and also to increase the porosity obtained after thermal treatment of the roofing granules.

The use of polyvinyl alcohol is not necessary to have a photocatalytic effect of granules. By consequence, a photocatalytic solution can be obtained without the addition of polyvinyl alcohol. The porosity of the layer can be provided by the space between colloidal silica particles.

Figure 7:
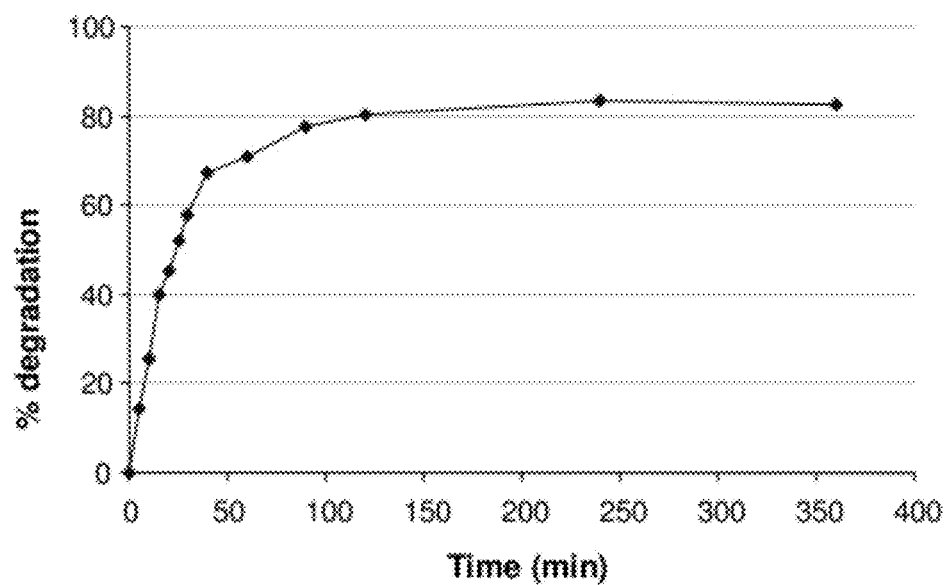
FIG. 7 is a graph showing the photocatalytic effect of an embodiment of roofing granules according to the present invention.

A discoloration test (with rhodamine solution) was carried out on shingle samples treated with colloidal silica embedded titanium dioxide (without adding polyvinyl alcohol). The results of this test are given in Table 4 and FIG. 7 (for ΔE variation).

TABLE 4

| Time (min) UV-A | ΔE | ΔE (% degradation) |
|---|---|---|
| 0 | 17.83 | 0.00 |
| 5 | 15.29 | 14.27 |
| 10 | 13.30 | 25.41 |

TABLE 4-continued

| Time (min) UV-A | ΔE | ΔE (% degradation) |
|---|---|---|
| 15 | 10.75 | 39.70 |
| 20 | 9.77 | 45.24 |
| 25 | 8.59 | 51.82 |
| 30 | 7.48 | 58.05 |
| 40 | 5.84 | 67.24 |
| 60 | 5.17 | 71.02 |
| 90 | 4.03 | 77.43 |
| 120 | 3.53 | 80.20 |
| 240 | 2.97 | 83.34 |
| 360 | 3.14 | 82.40 |

Figure 8:
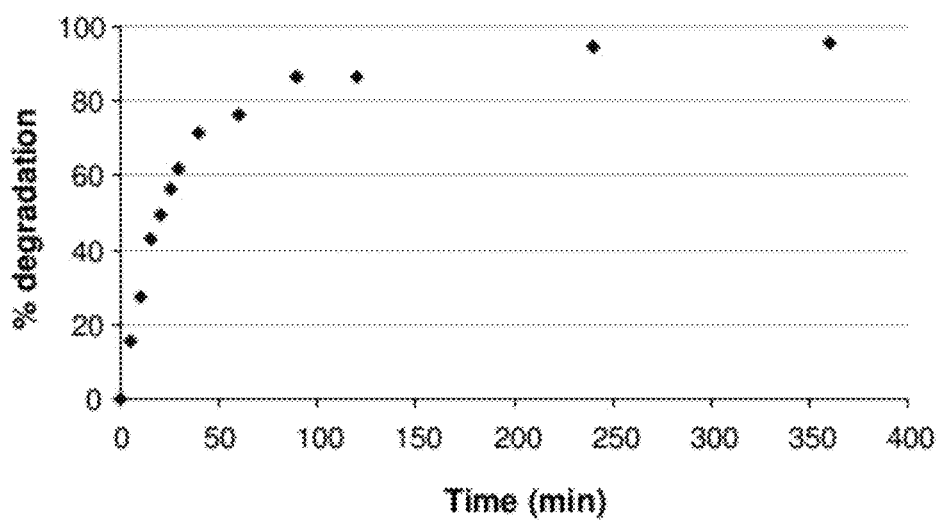
FIG. 8 is a graph showing the photocatalytic effect of an embodiment of roofing granules according to the present invention.

The variation of a* can also be monitored using the colorimetric test. As rhodamine has pink color, a* is thus the most varied when the sample is exposed under UV-A. Table 5 gives the variation of a* values for the same sample obtained in Table 4. These values are plotted in FIG. 8.

TABLE 5

| Time (min) | a* | Δa* (% degradation) |
|---|---|---|
| 0 | 16.65 | 0 |
| 5 | 14.07 | 15.50 |
| 10 | 12.08 | 27.43 |
| 15 | 9.48 | 43.04 |
| 20 | 8.44 | 49.29 |
| 25 | 7.23 | 56.58 |
| 30 | 6.32 | 62.06 |
| 40 | 4.73 | 71.61 |
| 60 | 3.96 | 76.22 |
| 90 | 2.77 | 86.36 |
| 120 | 2.20 | 86.81 |
| 240 | 0.90 | 94.57 |
| 360 | 0.70 | 95.80 |

In effect, it is more interesting to follow the variation of a* rather than ΔE because a* relates directly to the pink color of rhodamine.

Various modifications can be made in the details of the various embodiments of the processes, compositions and articles of the present invention, all within the scope and spirit of the invention and defined by the appended claims.

The invention claimed is:

1. A process for preparing biocidal roofing granules, the process comprising:
   (a) providing a mineral core;
   (b) preparing a gel-forming inorganic sol coating medium;
   (c) providing at least one biocidal photocatalytic metal oxide;
   (d) coating the mineral core with the inorganic sol coating medium;
   (e) forming a porous coating layer on the mineral core from the inorganic sol coating medium, the porous coating layer having a pore network; and
   (f) disposing the at least one photocatalytic metal oxide in the pore network.

2. A process according to claim 1 wherein the gel-forming inorganic coating medium is selected from the group consisting of silica sol-gels, colloidal silica media, colloidal zirconia media, colloidal titania media, and colloidal alumina media.

3. A process according to claim 1 wherein the coating medium is an aqueous suspension prepared from at least one precursor selected from the group consisting of alkylsilanes, alkoxysilanes, zirconium oxychloride, zirconium alkoxides, titanium chloride, titanium alkoxides, aluminum chloride, aluminum alkoxides, sodium silicate, potassium silicate, pyrogenic silica, pyrogenic alumina, pyrogenic titania, pyrogenic zirconia, and mixtures thereof.

4. A process according to claim 3 wherein the at least one precursor is selected from the group consisting of tetramethoxysilane, tetraethoxysilane, and methyl triethoxysilane.

5. A process according to claim 1, wherein the coating medium further comprises the at least one biocidal photocatalytic material.

6. A process according to claim 1 wherein the biocidal roofing granules further comprise a second biocidal composition selected from the group consisting of inorganic biocides and organic biocides.

7. A process according to claim 1 wherein the porous coating network is formed by drying the coating medium.

8. A process according to claim 7 wherein the coating medium is dried out at a temperature between about 10 and 100 degrees C.

9. A process according to claim 1 wherein the coating medium further comprises at least one sacrificial template material.

10. A process according to claim 9 wherein the sacrificial template material is selected from the group consisting of multiblock polyalkylene oxide materials, polyvinyl alcohol, and quaternary ammonium salts.

11. A process according to claim 9 wherein the sacrificial template material is a polyethyleneoxide-polypropyleneoxide-polyethyleneoxide triblock material.

12. A process according to claim 9 wherein the sacrificial template material is cetyl trimethylammonium bromide.

13. A process according to claim 1, wherein the coating medium further includes a sacrificial template material, and wherein forming the porous network comprises calcining the sol at a temperature from about 200 degrees C. to 1000 degrees C., before disposing the at least one photocatalytic metal oxide in the porous network.

14. A process according to claim 13 wherein the sacrificial template material is an organic polymer.

15. A process according to claim 1 wherein the at least one photocatalytic metal oxide is disposed in the porous inorganic layer by applying a suspension of the at least one photocatalytic material in a liquid carrier material to the porous inorganic layer, and evaporating the carrier material.

16. A process for preparing roofing materials, the process comprising:
   (a) providing a base material;
   (b) preparing a gel-forming inorganic coating medium;
   (c) providing at least one biocidal photocatalytic metal oxide;
   (d) coating the base material with the inorganic coating medium;
   (e) forming a porous coating layer on the mineral core from the inorganic coating medium, the porous coating layer having a pore network; and
   (f) disposing the at least one photocatalytic metal oxide in the pore network.

17. A process according to claim 16 wherein the gel-forming inorganic coating medium is selected from the group consisting of silica sol-gels, colloidal silica media, colloidal zirconia media, colloidal titania media, and colloidal alumina media.

18. A process according to claim 16 wherein the coating medium is an aqueous suspension prepared from at least one precursor selected from the group consisting of alkylsilanes, alkoxysilanes, zirconium oxychloride, zirconium alkoxides, sodium silicate, potassium silicate, titanium chloride, titanium alkoxides, aluminum chloride, aluminum alkoxides, pyrogenic silica, pyrogenic alumina, pyrogenic titania, pyrogenic zirconia, and mixtures thereof.

19. A process according to claim 18 wherein the coating medium further comprises a second biocidal composition selected from the group consisting of inorganic biocides and organic biocides.

20. A process according to claim 18 wherein the coating medium is dried out at a temperature between about 10 and 100 degrees C.

21. A process according to claim 20 wherein the coating medium is dried out a temperature between about 20 and 80 degrees C.

22. A process according to claim 20 wherein the coating medium comprises a sacrificial template and the sacrificial template material comprises an organic polymer.

23. A process according to claim 20 wherein the at least one photocatalytic metal oxide is disposed in the porous inorganic layer by applying a suspension of the at least one photocatalytic material in a liquid carrier material to the porous inorganic layer, and evaporating the carrier material.

24. A process according to claim 18 wherein the base material is selected from roofing shingles, roofing membranes and roofing granules.

25. A process according to claim 18 wherein the at least one precursor is selected from the group consisting of tetramethoxysilane, tetraethoxysilane, and methyl triethoxysilane.

26. A process according to claim 18, wherein the coating medium further comprises the at least one biocidal photocatalytic metal oxide.

27. A process according to claim 18 wherein the porous coating network is formed by drying the coating medium.

28. A process according to claim 18 wherein the coating medium further comprises at least one sacrificial template material.

29. A process according to claim 28 wherein the sacrificial template material is selected from the group consisting of multiblock polyalkylene oxide materials, polyvinyl alcohol, and quaternary ammonium salts.

30. A process according to claim 28 wherein the sacrificial template material is a polyethyleneoxide-polypropyleneoxide-polyethyleneoxide triblock material.

31. A process according to claim 28 wherein the sacrificial template material is cetyl trimethylammonium bromide.

* * * * *